United States Patent [19]

Uebayashi

[11] Patent Number: 4,971,735

[45] Date of Patent: Nov. 20, 1990

[54] FABRICATING METHOD OF RESIN BASE DENTURE

[76] Inventor: Noboru Uebayashi, 278-24, Kushiya-cho, Kumano-shi, Mie-ken, Japan

[21] Appl. No.: 385,003

[22] Filed: Jul. 25, 1989

Related U.S. Application Data

[60] Division of Ser. No. 385,002, Jul. 25, 1989.

[30] Foreign Application Priority Data

Jul. 29, 1988 [JP] Japan .................................. 63-190874
Dec. 14, 1988 [JP] Japan .................................. 63-315993

[51] Int. Cl.⁵ .............................................. A61C 13/00
[52] U.S. Cl. .......................................... 264/17; 264/25
[58] Field of Search ................ 264/17, 25, 26, 331.11, 264/18; 425/174, 174.2, 174.6, 174.8 R; 433/199.1, 171, 167

[56] References Cited

U.S. PATENT DOCUMENTS 2,472,492 7/1949 Saffir ....................................... 264/17
2,491,147 12/1949 Zahn ....................................... 264/17
4,390,482 6/1928 Feurer ...................................... 264/1.4

FOREIGN PATENT DOCUMENTS 269037 4/1927 United Kingdom ................... 264/17

Primary Examiner—James Lowe
Assistant Examiner—Christopher A. Fiorilla
Attorney, Agent, or Firm—Koda & Androlia

[57] ABSTRACT

A method of fabricating a resin base denture. The method includes: burying a wax denture in an investment in a tubular flask; removing the wax of the wax denture to form a hollow space; filling the space with resin; immersing the flask in water; and polymerizing the resin by microwave irradiation; thereby fabricating a resin base denture. When immersing the flask filled with resin in water, the lids are detected from the flask so that the investment is in direct contact with water.

2 Claims, 4 Drawing Sheets

FABRICATING METHOD OF RESIN BASE DENTURE

This is a division of application Ser. No. 385,002, filed Jul. 25, 1989.

BACKGROUND OF THE INVENTION

1. Field of Invention

This invention relates to a fabricating method of resin base denture in the field of dental technique.

2. Prior Art

As the method for easily fabricating a resin base denture, hitherto, it is known to polymerize the resin base by microwaves by using a microwave oven for cooking. In this method, since the resin base may be polymerized in a short time, the fabrication time of resin base denture may be remarkably shortened.

The apparatus used in manufacture of resin base denture, conventionally, is wholly or partly made of synthetic resin, and comprises a two-half flask in two layers, a top lid for covering the upper opening of the flask, and a bottom lid for covering the lower opening of the flask, in which the two elements are separably joined with bolt and nut fitting parts formed at proper positions on the side wall.

However, in the above method of polymerizing the resin base by microwaves, foams may be formed in the resin base depending on the type of investment, the dryness of investment, water mixing ratio, or when porcelain teeth are used. Also, when a metallic clasp or bar is used, the resin may whiten. Such shortcomings have been compensated for by using an exclusive resin, but such an exclusive resin is expensive, and the variety of colors is limited.

Still more, in the conventional fabricating method of resin base denture, a difference is likely to occur in the degree of polymerization between the thick portion and thin portion of the resin base, and even if the flask is turned upside down in the midst of polymerization in order to prevent this, uneven polymerization is inevitable. Besides, two or more conventional flasks for microwave (whether made of metal or synthetic resin), can not be put into an ordinary microwave oven, and if put in by force, all flasks are not uniformly irradiated with microwaves, and uneven polymerization would occur.

SUMMARY OF THE INVENTION

This invention is devised in the light of the above background, and it is hence a primary object thereof to present a fabricating method and apparatus of resin base denture capable of polymerizing the resin uniformly without any risk of excessive polymerization.

It is another object of the invention to present a fabricating method and apparatus of resin base denture capable of preventing uneven polymerization or deformation of the fabricated resin base by shortening the cooling time of the resin.

To achieve these and other objects disclosed in the following detailed description and the claims, the method of the invention is characterized by immersion of tubular flask in water when polymerizing the resin by microwave irradiation. By thus immersing the tubular flask in water, water penetrates into the investment, and this water is heated simultaneously when polymerizing the resin by microwave irradiation and the heat of this water is also applied to the resin from outside, so that the resin may be polymerized uniformly. Moreover, by this water, excessive polymerization of the resin may be prevented at the same time.

As an advantageous development of this invention, after allowing the tubular flask to cool, a step of cooling the resin by force by using coolant may be added. As a result, the cooling time may be shortened.

An important feature of the apparatus of the invention is that the tubular flask is made of metal, so that the tubular flask may be reduced in size. Besides, the top lid and the bottom lid of the tubular flask are detachable, and when the both lids are removed at the time of polymerization of resin and the tubular flask is immersed in water, water easily penetrates into the investment, and the resin is polymerized uniformly, while the cooling time of the resin may be also cut short.

Other features and benefits of the invention will be better understood and appreciated from the following detailed description taken in conjunction with the accompanying drawings.

BRIEF DESCRIPTION OF THE DRAWINGS

FIG. 1 shows a step of burying a wax denture into the investment in a tubular flask, FIG. 2 shows a step of forming a hollow space in the denture base by removing the wax of the wax denture, FIG. 3 shows a step of filling the denture base hollow space with resin, FIG. 4 shows a step of polymerizing the resin in the tubular flask by microwave irradiation, and FIG. 5 shows a step of cooling the tubular flask by force using a coolant.

DETAILED DESCRIPTION OF THE INVENTION

Figure 1:
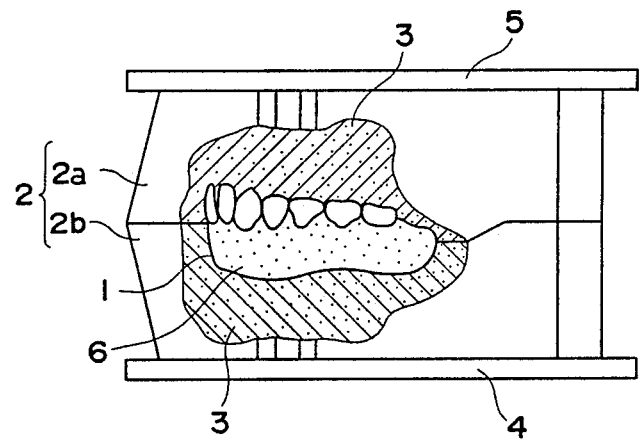
FIG. 1 to FIG. 5 are explanatory drawings showing the steps of fabricating method of the resin base denture of the invention.

Referring now to the drawings, an embodiment of fabricating method and apparatus of resin base denture according to the invention is described in details below.

FIG. 1 to FIG. 4 are process drawings showing the method of this invention.

FIG. 1 shows a step of burying a prepared wax denture 1 into an investment 3 in a tubular flask 2.

In this embodiment, the tubular flask 2 is in two layers, and the operating procedure is as follows. First, the lower opening of a lower element 2b of the tubular flask is covered with a bottom lid 4, and the lower element 2b is filled with the investment 3 such as gypsum, and the wax denture 1 is buried in this investment 3. Next, an upper element 2a of the tubular flask is put on the lower element 2b of the tubular flask, and this upper element 2a is also filled with the investment 3 such as gypsum, and the upper opening is covered with a top lid 5.

Figure 2:
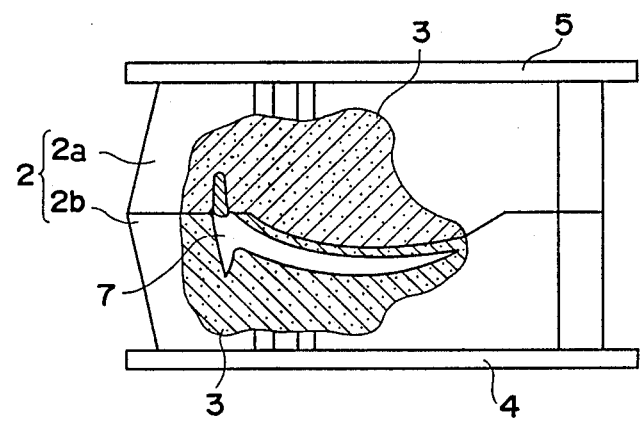

FIG. 2 relates to a step of forming a denture base hollow space in the investment 3 by softening the wax 6 of the wax denture 1 and removing it from the investment 3. In this step, first, the two-layer tubular flask 2 is dipped in warm water. Next, when the wax 6 in the wax denture 1 is softened, the tubular flask 2 is taken out of the warm water, and the two elements 2a, 2b of the tubular flask are separated, and the wax 6 is removed from the investment 3. Again, the two elements 2a, 2b are coupled together, and a denture base hollow space 7 is formed in the investment 3.

Figure 3:
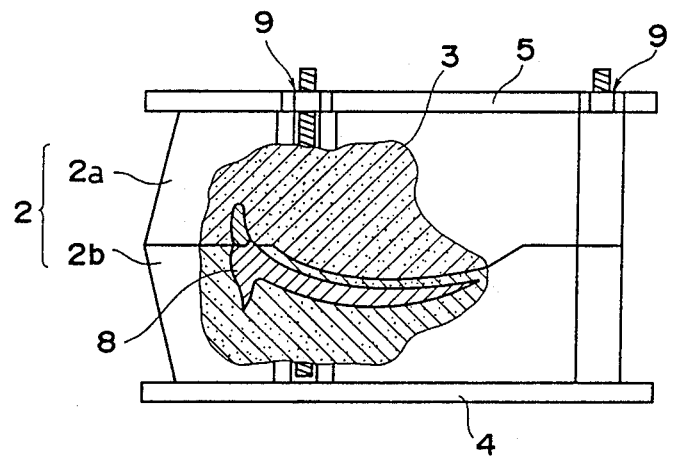

FIG. 3 shows a step of filling the denture base hollow space 7 with a dough-formed resin 8. In this step, first, the tubular flask 2 is separated, and the dough-formed resin 8 is built up in the denture base hollow space 7 at the investment 3 side of the upper element 2a to fill up.

Then the two elements 2a, 2b are put together and tightened by bolts and nuts 9 to pressurize the resin 8 in the tubular flask 2.

Figure 4:
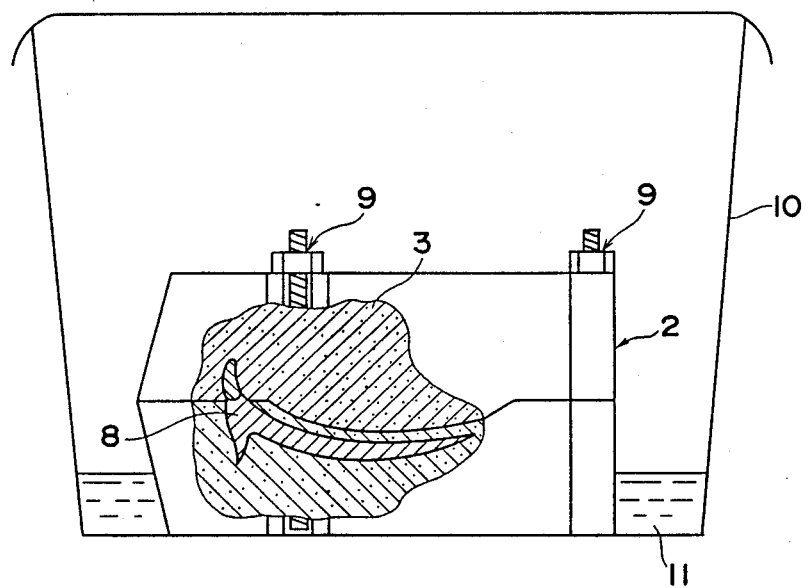

FIG. 4 is a step of polymerizing the resin 8 by microwave irradiation by immersing the tubular flask 2 in water. In this step, first, the top lid 5 and the bottom lid 4 of the tubular flask 2 are removed, and this tubular flask 2 is put into a container 10 made of synthetic resin. Hot or warm water 11 is poured into the container 10 to a height of 5 to 10 mm, and the container is put into a microwave oven (high frequency output 500W). When using an ordinary heat-polymerization resin, microwaves are emitted for about 4 minutes to polymerize the resin 8.

When putting two or more flasks in the oven, the microwave irradiation time is about 7 minutes for two flasks, about 9 minutes for three flasks, and about 12 minutes for four flasks. When a short-time heat-polymerization resin, ACRON MC (a tradename of GC Industrial Corp.) is used, the microwave irradiation time is 2 to 5 minutes for one to four flasks.

Incidentally, between the steps shown in FIGS. 3 and 4, an step of leaving the tubular flask 2 in hot or warm water for several minutes may be also inserted.

In the method described herein, by immersing the tubular flask 2 in water, water penetrates into the investment, and when polymerizing the resin 8 by microwave irradiation, this water is heated at the same time, and the heat is also applied to the resin 8 from outside, so that the resin 8 may be polymerized uniformly. Still more, excessive polymerization of the resin 8 is prevented by this water, and therefore any difference in the degree of polymerization does not occur between the thick portion and thin portion of the resin base, and foams are not formed inside the resin base, thereby preventing the resin 8 from whitening or lowering in the mechanical strength.

Figure 5:
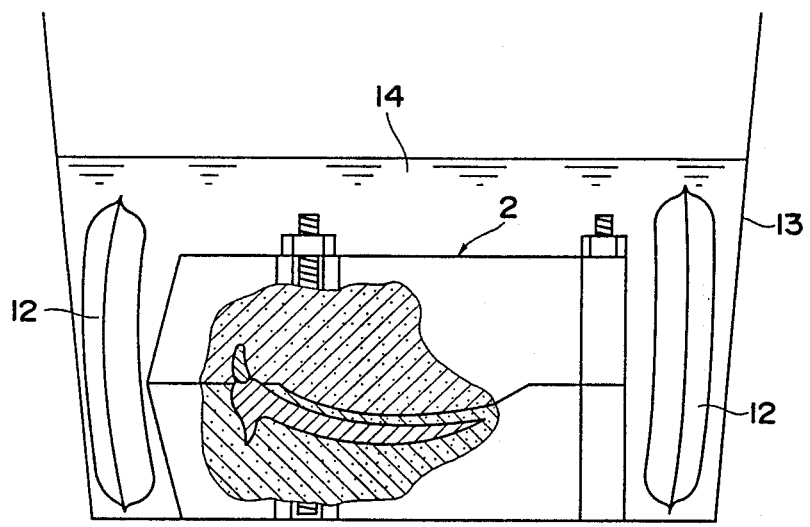

Furthermore, to the steps shown in FIG. 1 to FIG. 4, another step as shown in FIG. 5 may be added, that is, after allowing the tubular flask 2 to cool, the resin 8 may be cooled by force by using a coolant 12. In this step, first, the tubular flask 2 is allowed to cool, and is put into a proper container 13, and water 14 is poured into the container 13 until the tubular flask 2 is entirely immersed, and then a proper coolant 12 is put therein to cool the resin 8 by force until the resin is cooled sufficiently to the inside.

By thus cooling the resin 8 by force with the aid of the coolant 12, the cooling time is shortened, so that deformation of the resin base due to insufficient cooling after polymerization may be prevented.

Figure 6:
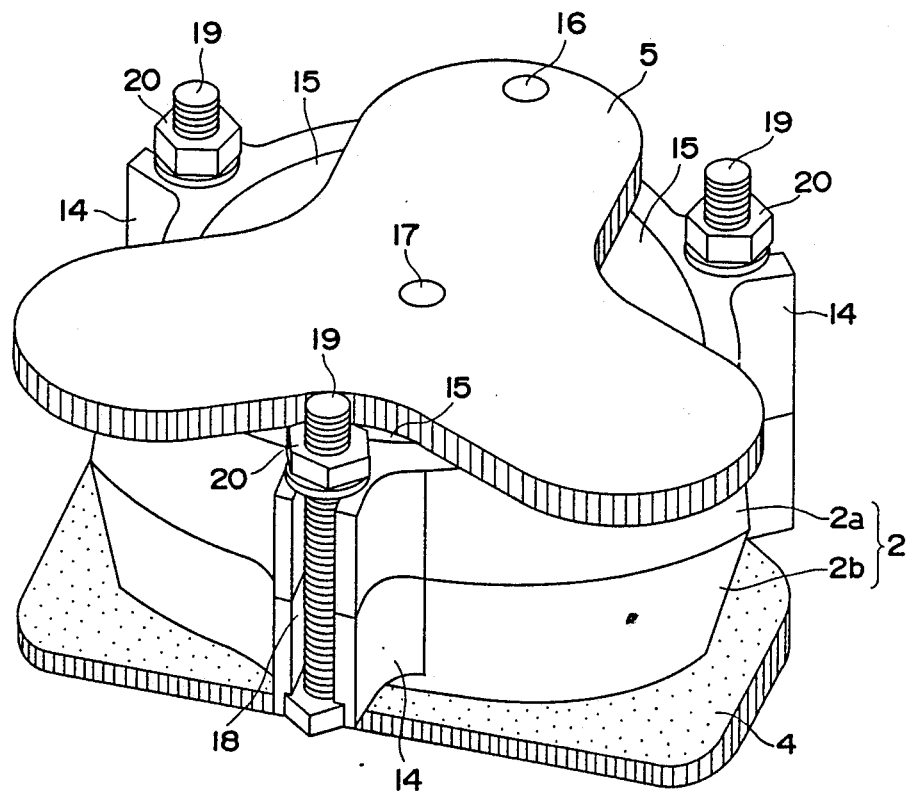
FIG. 6 is a perspective view of a fabricating apparatus of the resin base denture of this invention.

FIG. 6 is a perspective view showing a fabricating apparatus of resin base denture of this invention. This apparatus comprises a two-half tubular flask 2 in two layers, a top lid 5 for covering the upper opening of an upper element 2a of the tubular flask, and a bottom lid 4 for covering the lower opening of a lower element 2b of the tubular flask. At three positions on the side walls of the both elements 2a, 2b, junction means fitting parts 14 are disposed. In this embodiment, as the junction means of the upper and lower elements 2a, 2b, bolts and nuts are used. The top lid 5 and the bottom lid 4 can be detached when polymerizing the resin 8.

The tubular flask 2 is made of metal (e.g. aluminum alloy), and is fabricated by die-casting or other method. Meanwhile, the tubular flask 2 has a horizontal section of an approximately triangular shape with the corners being cut off, and is in a form smoothly fitting to a hand.

The top lid 5 is shaped so that a gap 15 may be formed at three positions at the corners of the upper opening of the tubular flask 2. When the top lid 5 covers the upper opening of the upper tubular flask 2a, it is held in the tubular flask 2 by the gypsum oozing out of the gaps 15. At one end of the top lid 5, there is a hole 16 so as to be easily held by gypsum forceps. Furthermore, nearly in the middle of the top lid 5, there is a hole 17 for using a resin injector. This hole 17 is, when the resin injector is not used, filled up with gypsum so as to play a role of holding means of the top lid 5 to the tubular flask 2. Or it may be also possible to form only several holes 17 without forming gaps 15, so that the top lid 5 may be held to the tubular flask 2 by the gypsum oozing out from these holes 17.

The bottom lid 4 is made of acrylic material and is reduced in weight, and the surface is smooth, and therefore the job is easy and adhesion to gypsum is excellent. The bottom lid 4 is in such a shape as to cover the entire lower opening of the lower element 2b of the tubular flask.

At the junction means fitting parts 14, there are fitting grooves 18 with the outer side opened. Even in a state of putting bolts 19 into nuts 20, they can be fitted into the fitting grooves 18 or taken out of the fitting grooves 18.

In this apparatus, the size is reduced because the tubular flask 2 is made of metal, and two or more flasks 2 may be put into an oven for polymerization without being stacking, so that all flasks 2 may be uniformly irradiated with microwaves according to the method described herein, thereby avoiding uneven polymerization.

Moreover, since the top lid 5 and the bottom lid 4 of the tubular flask 2 are designed detachable when polymerizing the resin, immersing the tubular flask 2 in water may faciliate water penetration into the investment, so that the resin may be polymerized uniformly. Furthermore, excessive polymerization of the resin is prevented by this water, and the cooling time is shortened when cooling the resin, and hence uneven polymerization of the resin base is prevented and deformation of resin base due to insufficient cooling after polymerization is avoided at the same time.

The embodiment of the invention illustrated herein is one of the preferred embodiments of the invention, and numerous changes and modifications of the shape, size and other conditions of the parts and others may be possible without departing from the true spirit of the invention or the scope of the claims thereof.

What is claimed is:

1. A method for fabricating a resin base denture comprising:
   a. burying a wax denture into an investment in a tubular flask,
   b. forming a denture base hollow space in said investment by softening the wax in said wax denture and removing from the investment,
   c. filling said denture base hollow space with a dough-formed resin,
   d. immersing said tubular flask with said hollow space in said investment filled with resin in water and allowing said water to penetrate said investment, and
   e. polymerizing said resin by means of microwave irradiation while said tubular flask is immersed in said water.

2. A method for fabricating a resin base denture according to claim 1 which further comprises;
   f. cooling the resin by force using a coolant after allowing said resin to cool in said tubular flask.

* * * * *